United States Patent
Losa Dominguez et al.

(10) Patent No.: US 11,524,039 B2
(45) Date of Patent: Dec. 13, 2022

(54) **TOPICAL COMPOSITIONS COMPRISING EXTRACT OF *CORIOLUS* VERSICOLOR FOR AUTOIMMUNITY ENHANCEMENT**

(71) Applicant: PROCARE HEALTH IBERIA, S.L., Castelldefels (ES)

(72) Inventors: Fernando Losa Dominguez, Barcelona (ES); Santiago Palacios, Madrid (ES); Yann Gaslain, Castelldefels (ES)

(73) Assignee: PROCARE HEALTH IBERIA, S.L., Castelldefels (ES)

( * ) Notice: Subject to any disclaimer, the term of this patent is extended or adjusted under 35 U.S.C. 154(b) by 222 days.

(21) Appl. No.: 17/112,778

(22) Filed: Dec. 4, 2020

(65) Prior Publication Data
US 2021/0085738 A1    Mar. 25, 2021

Related U.S. Application Data

(63) Continuation of application No. 15/124,656, filed as application No. PCT/EP2015/055349 on Mar. 13, 2015, now Pat. No. 10,874,702.

(30) Foreign Application Priority Data

Mar. 13, 2014 (EP) .................................. 14159640

(51) Int. Cl.
| | |
|---|---|
| *A61K 36/07* | (2006.01) |
| *A61K 36/23* | (2006.01) |
| *A61K 36/58* | (2006.01) |
| *A61K 9/06* | (2006.01) |
| *A61K 9/00* | (2006.01) |
| *A61K 31/05* | (2006.01) |
| *A61K 31/716* | (2006.01) |
| *A61K 31/728* | (2006.01) |
| *A61K 36/886* | (2006.01) |
| *A61K 45/06* | (2006.01) |

(52) U.S. Cl.
CPC ............ *A61K 36/07* (2013.01); *A61K 9/0034* (2013.01); *A61K 9/06* (2013.01); *A61K 31/05* (2013.01); *A61K 31/716* (2013.01); *A61K 31/728* (2013.01); *A61K 36/23* (2013.01); *A61K 36/58* (2013.01); *A61K 36/886* (2013.01); *A61K 45/06* (2013.01); *Y02A 50/30* (2018.01)

(58) Field of Classification Search
None
See application file for complete search history.

(56) References Cited

U.S. PATENT DOCUMENTS

| | | |
|---|---|---|
| 8,076,311 B2 | 12/2011 | Prendergast |
| 8,916,541 B2 | 12/2014 | Eliaz |
| 2008/0124303 A1 | 5/2008 | King |
| 2008/0241317 A1 | 10/2008 | Viana |
| 2009/0130138 A1 | 5/2009 | Stamets |
| 2009/0181047 A1 | 7/2009 | Bishop et al. |
| 2012/0164121 A1 | 6/2012 | Paufique |
| 2014/0017275 A1 | 1/2014 | Lau et al. |

FOREIGN PATENT DOCUMENTS

| | | |
|---|---|---|
| CN | 1209954 A | 3/1999 |
| EP | 2522356 A2 | 11/2012 |
| JP | 2012/075390 A | 4/2012 |
| KR | 2006/097847 A | 9/2006 |
| WO | WO2004080474 A1 | 9/2004 |
| WO | WO2006134409 A2 | 12/2006 |
| WO | WO 2008010241 A1 | 1/2008 |
| WO | WO2011094579 A2 | 8/2011 |
| WO | WO2012046145 A2 | 4/2012 |

OTHER PUBLICATIONS

Kang, et al., "Effects of βglucans from *Coriolus versicolor* on macrophage phagocytosis are related to the Akt and CK2/Ikaros," International Journal of Biological Macromolecules, 2013, vol. 57: pp. 9-16.

Cui, Jian and Yusuf Chisti, "Polysaccharopeptides of *Coriolus versicolor*: physiological activity, uses, and production," Biotechnol Adv., 2003, vol. 21: pp. 109-122.

Cheng, King-Fai and Ping-Chung Leung, "General review of polysaccharopeptides (PSP) from. *C. versicolor*: Pharmacological and clinical studies," Cancer Therapy, 2008, vol. 6: pp. 117-130.

"Assessment report on *Centella asiatica* (L.) Urban, herba," EMA/HMPC/291177/2009, Nov. 25, 2010 (44 pages).

Tiwari, et al., "In vitro Antiviral Activity of Neem (*Azardirachta indica* L.) Bark Extract against Herpes Simplex Virus Type-1 Infection," Phytotherapy Research, 2010, vol. 24: pp. 1132-1140.

"Biological evaluation of medical devices, Part 10: Tests for irritation and skin sensitization," ISO 10993-10, Aug. 1, 2010 (74 pages).

"Biological evaluation of medical devices, Part 5: Tests for in vitro cytotoxicity," ISO 10993-5, Jun. 1, 2009 (42 pages).

Strum, et al., "Tissue Expression Profiling Using Real-Time PCR," Current Protocols in Pharmacology, 2002, Supplement 18: pp. 6.9.1-6.9.9.

Bachmann, G., "Urogenital ageing: an old problem newly recognized," Maturitas, 1995, vol. 22 Supplement: pp. S1-S5.

Bachmann, G., "A new option for managing urogenital atrophy in post menopausal women," Contemporary OB/GYN Apr. 15, 1997, vol. 42, No. 12 pp. 13-28.

(Continued)

*Primary Examiner* — Michael Barker
(74) *Attorney, Agent, or Firm* — Squire Patton Boggs (US) LLP (57) ABSTRACT

The present invention provides a topical composition comprising extract from *Coriolus versicolor* for use for preventing and/or treating by vaginal or cervical administration of a vaginal or cervical disorder which is caused by an infectious agent, in particular, human papiloma virus infections and related disorders, including cervical cancer. The composition of the invention acts enhancing genital immunity against infectious agents and re-epithelising damaged tissue.

8 Claims, 4 Drawing Sheets

(56) References Cited

OTHER PUBLICATIONS

Mycology Research Laboratories, "Clinical Trial Results Show Proof-of-Concept For Use Of Coriolus Versicolor As Immunonutrition In HPV Patients With Cervical Lesions (LSIL)," XP002727390, Apr. 29, 2008, retrieved from internet on Jul. 15, 2014: URL: http://www.medicalnewstoday.com/releases/105573.php (4 pages).

Database WPI / Thomson Scientific, XP002738435, 2003, KR 2003 0082619 A abstract (1 page).

Kawana, Takashi and Madoka Hashido, "Treatment of Recurrent Genital Herpes with PSK," International Journal of Immunopharmacology, 1988, vol. 10: pp. 152 (abstract only).

International Search Report and Written Opinion for PCT/EP2015/055349, dated Apr. 28, 2015 (14 pages).

Ray, et al: "Modulation of humoral and cell-mediated immune responses by *Azadirachta indica* (Neem) in mice", Indian Journal of Experimental Biology, Jul. 1996, vol. 34, pp. 698-701.

Sairam, et al: "Anti-micorbial activity of a new vaginal contraceptive NIM-76 from neem oil (*Azidirachta indica*)", Journal of Ethnopharmacology 2000, vol. 71, pp. 377-382.

TOPICAL COMPOSITIONS COMPRISING EXTRACT OF *CORIOLUS* VERSICOLOR FOR AUTOIMMUNITY ENHANCEMENT

CROSS-REFERENCE TO RELATED APPLICATION

This application is a continuation of U.S. patent application Ser. No. 15/124,656, filed Sep. 8, 2016, which is a U.S. national phase entry of International Patent Application No. PCT/EP2015/055349, filed Mar. 13, 2015, which in turn claims priority to European Patent Application No. 14159640.3, filed Mar. 13, 2014. Each of the foregoing applications is incorporated herein by reference in its entirety.

The present invention relates to the field of genital disorders, particularly gynecological disorders caused by infectious agents. The invention provides topical compositions for use in the prevention and/or treatment of such disorders.

BACKGROUND ART

Gynecological infections are common among women of all ages. Typical gynecological infections include bacterial vulvovaginitis, vaginal yeast infection, trichomoniasis, ine-specific vulvovaginitis and viral infection. Viral infections are among the hardest to treat. In particular, human papilloma virus (HPV) infection, which may cause cervical cancer, is an increasing source of concern, particularly among sexually active women.

Cervical cancer caused by HPV infection has become the 2nd most common female cancer in women aged 15 to 44 in some developed countries. More 20 than 30 to 40 types of HPV are typically transmitted through sexual contact and infect the anogenital region. However, most HPV types do not cause disease. Persistent infection with "high-risk" HPV types may progress to pre-cancerous lesions and invasive cancer.

HPV types 16 and 18 together cause about 70% of all cervical cancers. It is important to note, however, that the great majority of high-risk HPV infections are cleared by the hosts immune system and regress to subclinical in one year and ninety percent in two years. However, a minority of subjects (5% to 10% of infected women) fail to control viral infection and develop a persistent infection with HPV. As mentioned above, such persistent infections have a risk of developing precancerous lesions of the vulva and cervix, which can progress to invasive cancer.

Figure 1:
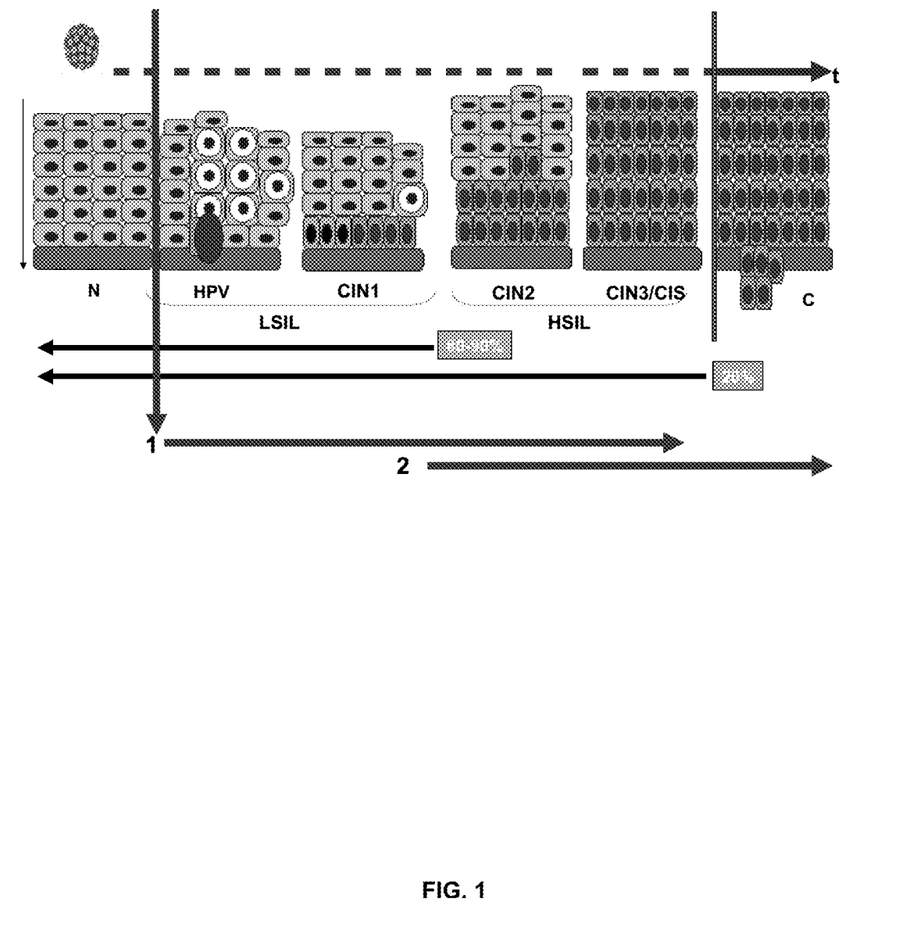

HPV lesions are thought to arise from the proliferation of infected basal keratinocytes. Infection typically occurs when basal cells in the host are exposed to infectious virus through a disturbed epithelial barrier as would occur during sexual intercourse or after minor skin abrasions. Once an HPV virion invades a cell, an active infection occurs, and the virus can be transmitted. Several months to years may elapse before squamous intraepithelial lesions (SIL) develop and can be clinically detected. Persistent infection favored by disturbed epithelial barrier favours cervical carcinogenesis. A comprehensive scheme of cervical cancer evolution is presented in FIG. 1.

Progression from subclinical to clinical infection may take years; providing opportunities for detection and treatment of pre-cancerous lesions. Progression to invasive cancer can be prevented when subclinical HPV infection is detected early and regular examinations are performed. To this effect, cervical screening using a Papanicolaou (Pap) test or liquid-based cytology is used to detect abnormal cells that may develop into cancer. If abnormal cells are found, women are invited to have a colposcopy. During a colposcopic inspection, biopsies can be taken and abnormal areas can be removed with a simple procedure, typically with a cauterizing loop or, more commonly in the developing world—by freezing (cryotherapy). Treating abnormal cells in this way can prevent them from developing into cervical cancer. Pap smears have reduced the incidence and fatalities of cervical cancer in the developed world, but even so the incidence of cervical cancer in these countries is not decreasing. Additionally, Paps screening is not commonly available for the majority of women in resource-poor areas, where cervical cancer also has substantial mortality.

It should also be taken into account that the results of the Pap test are often not conclusive and, in such cases, surgical intervention is not recommended, as it implies associated risks and elevated costs. An unconclusive Pap test occurs when abnormal cells of the type CIN1, which indicate mild cervical intraepithelial neoplasia, are detected. Usually when a biopsy detects CIN 1 the woman has an HPV infection which may clear on its own within 12-24 months, and thus is followed for later testing rather than treated. Women in this situation have no way of knowing what to expect and may not follow a preventive or therapeutical strategy, which often causes psychological stress and anxiety. A therapeutical or quirurgical strategy is only started when a later analysis shows a malignant evolution (usually first when type 2 cervical intraepithelial neoplasia, CIN2, is detected).

HPV vaccines (Cervarix and Gardasil), which prevent infection with the HPV types (16 and 18), may lead to further reduce the incidence of cervical cancer. However, although these preventive vaccines cover the two most common types of high risk HPV, other high risk viruses causing the remaining 30% of cervical cancer cases are not yet covered. Further, since HPV is the most common sexually transmitted disease, a vast number of individuals are already infected and as such can not profit from this preventive vaccination.

Altogether, there is currently a need to provide alternative strategies to combat HPV infection and cervical cancer, particularly at the early stages of HPV infection.

SUMMARY OF THE INVENTION

The present inventors have developed an strategy for combating HPV and other gynecological infections. The present strategy involves enhancing the local immunity of the genital system, particularly the vagina and cervix, by genitally administering a composition comprising extract from *Coriolus versicolor*.

The extract from *Coriolus versicolor* contains two beta-glucans, polysaccharide K (PSK) and polysaccharide-peptide (PSP), which have been described as effective immunopotentiators (Kang S C et al., *Int J Biol Macromol.* 2013, vol. 57, p. 9-16; Cui J, et al., *Biotechnol Adv.* 2003, vol. 21(2), p. 109-22).

Oral preparations containing said extract are known in the art and have been used, particularly in Japan, as coadjuvants for chemotherapy and radiotherapy of cancers and various infectious diseases. However, *C. versicolor* extract has not been previously used for local treatment of genital disorders caused by infectious agents, including HPV infection and cervical cancer. The inventors have currently found that the composition of the invention comprising extract of *Coriolus versicolor* is particularly effective in combating genital infections such as vaginitis and HPV infection when directly administered to the vulva, vagina and/or the cervix.

Thus, an aspect of the invention provides a topical composition comprising extract from *Coriolus versicolor* for use in the prevention and/or treatment by genital administration of a genital disorder which is caused by an infectious agent. The term "infectious agent" is understood as a microorganism, in the widest sense, such as a virus, bacterium, prion, fungus or protozoan, that causes disease in its host. In the present invention the term "infectious agent" and "pathogen" are used indistinctively.

The present strategy to combat HPV and other genital infections provides several advantages. First of all, by administering the active components of *Coriolus versicolor* (particularly PSK and PSP) directly to the site of action, a local enhancement of immunity is achieved. Since the genital system, mainly the vagina and cervix, is very sensitive to infectious diseases, enhancement of immunity in this particular environment is highly beneficial. The local boosting of genital immunity helps the body fight against all sorts of genital infections, from inespecific vaginitis and candidiasis to HPV infection. Secondary side effects may be minimised because the active components in the composition can be more easily adjusted to achieve the desired effect, at the same time that an optimal dose-respond may be achieved. Further, administration by vaginal/cervical route allows for an easy application and circumvents the need to protect the active compounds from hostile environments like the gastrointestinal tract.

Another aspect of the present invention provides a topical composition for genital administration comprising extract from *Coriolus versicolor*.

BRIEF DESCRIPTION OF THE DRAWINGS

FIG. 1. Carcinogenesis scheme for cervical cancer. N represents normal, non-infected epithelium. A women becomes infected by HPV and develops low squamous intraepithelial lesion (LSIL). Possibly no changes are be found in the epithelial cells during the first months of infection. Eventually, grade 1 cervical intraepithelial neoplasia (CIN1) may be observed. After 12 to 24 months the patient may develop high squamous intraepithelial lesion (HSIL). At first, grade 2 cervical intraepithelial neoplasia (CIN2) may be observed. Over the years this lesion may evolve to grade 3 cervical intraepithelial neoplasia (CIN3) and eventually to invasive carcinoma (C). Percentages indicate the estimated amount of patients for which the HPV infection will reach these stages. The arrow marked with "t" represents increasing time. The arrow marked with "↓" indicates the stage where preventive and screening strategies begin. The arrow marked with "1" indicates the stage where treatment of the affected patients begin.

DETAILED DESCRIPTION OF THE INVENTION

In the present application the term "extract" is used in the conventional sense to refer to concentrated preparations of compounds obtained by removing the active constituents from the source, usually a botanical source, with suitable means. Said extracts contain one or more active ingredients and may be incorporated in pharmaceutical or cosmetical compositions in a variety of forms, including a pure or semi-pure component, a solid or liquid extract, or a solid plant matter.

Usually botanical extracts contain not only one but multiple constituents, many of them active. Sometimes, the beneficial effect is derived from the combination of many of these active compounds. In other cases there is one particular compound that is mainly responsible for most of the activity.

The extract as used herein also includes "synthetic" extracts, i.e. various combinations of known components and/or constituents that are combined to substantially mimic the composition and/or activity of a botanical extract of natural origin. The synthetic extracts will have two or more, three or more, or four or more active ingredients in common with that of the natural source. Natural or synthetic extracts that are enriched in one or several components are also considered part of the present invention.

*Coriolus versicolor* (from now on *C. versicolor*, also known as *Trametes versicolor*) is a common polypore mushroom belonging to the family Basidiomycota found throughout the world. The visible form of *C. versicolor* is a fan-shaped mushroom with wavy margin and colored concentric zones. *C. versicolor* is an obligate aerobe that is commonly found year-round on dead logs, stumps, tree trunks, and branches.

By "extract of *Coriolus versicolor*" it is understood, as previously defined, a concentrated preparation of compounds obtained from *C. versicolor*. The main active compounds in *C. versicolor* extracts are beta-glucans polysaccharopeptide Krestin (PSK) and polysaccharopeptide (PSP). Both compounds are obtained from the extraction of *C. versicolor* mycelia.

"Extract from *C. versicolor*" as used herein generally refers to preparations containing biologically-active chemical constituents and/or compounds isolated from *C. versicolor*, preferably polysaccharopeptide Krestin (PSK) and/or polysaccharopeptide (PSP). This includes *C. versicolor* whole extracts but also pure or semi-pure preparations of the mentioned biologically-active compounds obtained from *C. versicolor*.

Extracts from *C. versicolor* containing biologically-active compounds and preparations containing the purified compounds are commercially available, for example through the company SYMRISE. Most commercial preparations of polysaccharopeptides use only the intracellular polymers recovered from the mushroom or submerged culture mycelium. Typical composition and extraction method for *C. versicolor* extract is described in Cui J et al, supra).

PSP and PSK are chemically similar beta-glucans polysaccharides linked to a number of proteins (K F Cheng, et al., *Cancer Therapy* 2008, vol. 6, p. 117-130) and they posses similar physiological activity profiles. These compounds are known as effective immunopotentiators and inhibitors of cancer proliferation (Kang S C et al., supra; Cui J, et al., supra).

The term "beta-glucan" in its widest sense refers to polysaccharides of D-glucose monomers linked by beta-glycosidic bonds. Beta-glucans are a diverse group of molecules that can vary with respect to molecular mass, solubility, viscosity, and three-dimensional configuration. Several beta-glucans have been described to have a variety of biological activities. In the present invention, the term "beta-glucan" is understood to refer to these biologically-active beta-glucans, particularly those derived from yeasts and biological mushrooms, including polysaccharopeptides from *C. versicolor*. Further biologically active beta-glucans are contemplated in the present invention, for instance, beta-glucans from other mushrooms such as reishi, shiitake, Chaga and maitake, β(1,3)D-glucan from bakers yeast, β(1,3)(1,4)-glucans from oats and barley. Beta-glucan derivatives, such as carboxymethyl beta-glucan are also comtemplated. These beta-glucans also have been reported as possessing immunomodulating properties. Carboxylated beta-glucans have been also described as having wound healing properties. A convenient source of beta-glucans is the product NIO-GLUCAN® from the company Naturalis Life Technologies. NIO-GLUCAN® contains carboxymethyl beta-glucan, magnolol and honokiol carried by niosomal vesicles.

The term "genital administration" as used herein refers to administration to external or internal genitals, particularly vulva, vagina or cervix, but also anus or rectum. In a particular embodiment, the genital administration is vaginal or cervical administration. In another particular embodiment the genital administration is rectal or anal administration.

As mentioned, an aspect of the invention provides a topical composition comprising extract from *Coriolus versicolor* for use in the prevention and/or treatment by genital administration of a genital disorder which is caused by an infectious agent. This aspect may be reformulated as use of a topical composition comprising extract from *Coriolus versicolor* for the preparation of a medicament for the prevention and/or treatment by genital administration of a genital disorder which is caused by an infectious agent. The invention also provides a method for prevention and/or treatment of a genital disorder which is caused by an infectious agent in an animal in need thereof, including a human, which comprises genitally administering a topical composition comprising extract from *Coriolus versicolor*.

In a preferred embodiment, the prevention and/or treatment comprises enhancing genital immunity against infectious agents.

It is considered part of the invention the provision of a topical composition comprising extract from *Coriolus versicolor* for use by genital administration in enhancing genital immunity against infectious agents. This aspect can be reformulated as use of a topical composition comprising extract from *Coriolus versicolor* for the preparation of a medicament for enhancing genital immunity against infectious agents by genital administration. The invention also provides a method for enhancing genital immunity against infectious agents in an animal in need thereof, including a human, which comprises genitally administering a topical composition comprising extract from *Coriolus versicolor*.

The topical composition for genital administration of the invention comprises an extract from *Coriolus versicolor*. The compositions of the invention can additionally incorporate other active ingredients which reinforce the beneficial effects of *C. versicolor* extract either by further boosting immunity, reducing inflammation, favoring a beneficial vaginal flora, repairing disturbed epithelial barrier or fighting undesired infectious agents. In this sense, the inventors have found that synergic interactions take place among the extract of *C. versicolor* and active compound selected from the group consisting of a moisturizing agent, a prebiotic, an antiinflammatory agent, a tissue regenerating agent and an antiviral agent. Thus, in one embodiment the topical composition according to the invention, in addition to extract from *C. versicolor*, further comprises at least an active compound selected from the group consisting of a moisturizing agent, a prebiotic, a tissue regenerating agent, an antiinflammatory agent and an antiviral agent.

*C. versicolor* extracts stimulate protective immune responses while suppressing unwanted immune responses that can cause disease. For instance, the *C. versicolor* extracts can restore or improve depressed immune system function, which is caused by, for example, the administration of anti-cancer agents. *C. versicolor* extracts can stimulate protective immune responses that defend against viral, bacterial, and/or microbial infection. In addition, the *C. versicolor* extracts can suppress unwanted immune responses, such as the production of TNF-a and its induction of metalloproteinase production, which are utilized by certain tumor cells to promote metastasis.

When administered directly to the genital area, particularly to the vulva, vagina or cervix, the topical composition according to the invention boosts local immune response to fight against typical pathogens that may be present in this area, such as human papiloma virus (HPV), *Candida albicans*, *Chlamydia trachomatis*, *Gardnerella vaginalis*, *Mobiluncus*, *Bacteroides*, *Mycoplasma*, *Neisseria gonorrhoeae*, *Trichomonas vaginalis*, Herpes virus, *Staphylococcus aureus*, *Staphylococcus epidermis*, *Escherichia coli*, *Streptococcus alpha*, *Bacillus*, *Enterobacter*, *Proteus*, *Enterobacter cloacae*, *Klebsiella*, *S. epidermidis*, *Kebsiella pneumoniae* and dermatophytes. These pathogens are responsible for a serious of disorders that include, in a non-limitative way, vaginitis, vulvovaginitis, dermatophytosis, candidiasis, genital herpes, gonorrhoea, proctitis, infertility, cervicitis, pelvic inflammatory disease, ectopic pregnancy, acute or chronic pelvic pain, trichomoniasis and cervical cancer. Thus in one embodiments the topical composition for genital administration of the invention is for use in the prevention and/or treatment of any of the above disorders.

In another particular embodiment the genital disorder to be prevented or treated by the composition of the invention is vaginitis. "Vaginitis" refers to an inflammation of the vagina usually due to infection which can result in discharge, itching and pain, and is often associated with an irritation or infection of the vulva. In the latter case the disorder is termed "vulvovaginitis".

Several types of vaginitis are known to commonly affect women, among them bacterial vaginitis, mycotic vaginitis, trichomoniasis, nonspecific vaginitis and viral vaginitis.

Mycotic vaginitis is caused by caused by a fungal infection, usually by overgrowth of the yeasts of the genus *Candida*, but can also be caused by dermatophyte infection. It is most commonly caused by a type of fungus known as *Candida albicans*. The *Candida* species of fungus is found naturally in the vagina, and is usually harmless. However, if the conditions in the vagina change, *Candida albicans* can cause the symptoms of thrush.

Trichomoniasis, sometimes referred to as "trich", is another common cause of vaginitis. It is a sexually transmitted disease, and is caused by the single-celled protozoan parasite *Trichomonas vaginalis* producing mechanical stress on host cells and then ingesting cell fragments after cell death. Symptoms include inflammation of the cervix (cervicitis), urethra (urethritis), and vagina (vaginitis) which produce an itching or burning sensation.

Nonspecific vaginitis is a disease of the vagina which is caused by an imbalance of naturally occurring bacterial flora. The microorganisms involved in bacterial vaginitis are very diverse, but include *Gardnerella vaginalis, Mobiluncus, Bacteroides*, and *Mycoplasma*. A change in normal bacterial flora including the reduction of Lactobacilli, which may be due to the use of antibiotics, hormonal changes or pH imbalance, allows such harmful bacteria to gain a foothold and multiply. This type of vaginitis is extremely common, particularly among women of child-bearing age.

Viruses are also common cause of vaginitis. One form caused by the herpes simplex virus (HSV) is often just called "herpes" infection. These infections also are spread by sexual contact. The primary symptom of herpes vaginitis is pain associated with lesions or "sores." These sores usually are visible on the vulva or the vagina but occasionally are inside the vagina and can only be seen during a gynecologic exam.

Another source of viral vaginal infection is the human papillomavirus (HPV). HPV, sometime referred to as genital warts, also can be transmitted by sexual intercourse. This virus can cause painful warts to grow in the vagina, rectum, vulva or groin.

As explained above, persistent infection of HPV may also cause cervical cancer. In a preferred embodiment, the topical composition of the invention is for enhancing genital immunity against HPV. In another preferred embodiment, the topical composition of the invention is for the prevention and/or treatment of cervical cancer.

In particular, the composition of the invention is beneficial for preventing persistent infection by HPV, thereby providing an effective strategy to fight against cervical cancer at an early stage where no other therapeutical strategy is available.

As mentioned above, therapeutical intervention up to date takes place at the stage where HSIL (High Squamous Intraepithelial Lesion) is detected. Patients showing no more than LSIL (Low Squamous Intraepithelial Lesion, coincident with cells of the type CIN1) are left untreated for a time ranging from 12 to 24 months, until tests are repeated and HSIL is confirmed (see FIG. 1). The composition of the invention is particularly useful for patients showing LSIL/CIN1 positive tests who nowadays receive no treatment. The composition of the invention may be administered at this stage and provide benefits in terms of helping the body clear HPV infection by locally increasing immunity and avoiding persistent HPV infection, as well as in terms of curing the mentioned LSIL/CIN1 lesions by enhancing re-epithelisation of the affected area. Thus in a particular embodiment the topical composition of the invention is for genital (vaginal or cervical) administration to women showing low squamous intraepithelial lesion (LSIL) or mild cervical intraepithelial neoplasia (CIN1). This embodiment can also be worded as a method for the prevention or treatment of HPV infection or cervical cancer by vaginal or cervical administration of the composition of the invention in a woman showing LSIL or CIN1.

The effective clearance of HPV infection at this stage is commonly known as "negativisation". Thus one embodiment of the invention is directed to the topical composition of the invention for use in negativising HPV positive women showing LSIL or CIN1 by vaginal or cervical administration. This embodiment can also be worded as a method for negativising HPV positive women showing LSIL or CIN1 by vaginal or cervical administration of the composition of the invention.

In another particular embodiment the composition of the invention is for use in curing vaginal epithelial lesions caused by an infectious agent, in particular LSIL or CIN1 lesions caused by HPV. In other words, the composition of the invention is useful for re-epithelisation of vaginal tissue damaged as a consequence of the infectious agent, in particular, for re-epithelisation of LSIL or CIN1 lesions caused by HPV.

Regardless of the above, the composition of the invention may be used in other pathological stages. For example the composition of the invention may be administered vaginally or cervically to women with Low Squamous Intraepithelial Lesion stages (either HPV or CIN1) for preventing persistent HPV infection and/or re-epithelization of vaginal lesions. The composition of the invention may also be used as adjuvant therapy for the treatment of women with HSIL or carcinoma.

A typical treatment regime for patients suffering from HPV infection comprises from 21 to 75 applications of the composition of the invention during six months. Thus in a particular embodiment the topical composition for genital administration is for use in the treatment of HPV infection, wherein the treatment regime comprises from 21 to 75 applications of the topical composition during 6 months. A typical treatment regime for patients suffering from other genital infections, particularly, recurrent genital infections, comprises from 7 to 21 applications of the composition of the invention during six months.

The topical composition for genital administration comprising an extract from *Coriolus versicolor* is part of the invention. In one embodiment the topical composition of the invention comprises a moisturizing agent. The term "moisturizing agent", also called "emollient", is used herein in its general sense in the art of pharmacy and cosmetic as a compound that increases or maintains skin or mucosal hydration. In a preferred embodiment, the moisturizing agent is hialuronic acid.

Hialuronic acid (HA, also called hyaluronan or hyaluronate, CAS Number 9004-61-9) is an anionic, nonsulfated glycosaminoglycan distributed widely throughout connective, epithelial, and neural tissues. HA is a polymer of disaccharides, themselves composed of D-glucuronic acid and D-N-acetylglucosamine, linked via alternating $\beta$-1,4 and $\beta$-1,3 glycosidic bonds. The presence of HA in epithelial tissue has been shown to promote keratinocyte proliferation and increase the presence of retinoic acid, causing skin hydration. Hyaluronic acid's interaction with CD44 drives collagen synthesis and normal skin function. Present in the extracellular matrix of basal keratinocytes, hyaluronic acid is critical to the structural integrity of the dermal collagen matrix. These benefits make hyaluronic acid a very effective topical moisturizer. Moreover, it has been described that HA may have benefits in wound repair. Moisturizing and wound repairing activities of HA are very convenient when combined with the immuno-enhancing activity of *C. versicolor* extract in the composition of the invention to fight persistent infection by HPV and also other infections causing, for example, vaginitis. HA is commercially available from multiple sources.

In one embodiment the topical composition of the invention also comprises a prebiotic. The term "prebiotic" is used herein in its general sense in the state of the art as non-digestible food ingredients that stimulate the growth and/or activity of animal-colonizing bacteria in ways claimed to be beneficial to health. This definition does not emphasize a specific bacterial group to be the target of the prebiotic. Generally, however, it is assumed that a prebiotic should increase the number and/or activity of bifidobacteria and lactic acid bacteria, both of which have several beneficial effects on the host, especially in terms of maintaining an equilibrated microfloral balance and the effectiveness and intrinsic strength of the immune system.

In a preferred embodiment, the prebiotic which is present in the composition of the invention is BioEcolia®. BioEcolia® is an alpha-glucan oligosaccharide obtained by enzymatic synthesis from natural sugars (sucrose and maltose). By virtue of the specificity of its glycosidic links, BioEcolia® is a bioselective substrate for beneficial microbial flora favouring the development of the skin's saprophytic flora to the detriment of undesirable opportunistic flora, pathogenic or not. This prebiotic is commercially available, for example from the company Solavia. Additional non-limiting prebiotics that are contemplated for use in the composition of the invention are fructooligosaccharides, galactooligosaccharides and inulin.

In one embodiment the topical composition of the invention further comprises a tissue regenerating agent. By "tissue regenerating agent" it is understood a compound that may promote renewal, restoration and/or growth of body tissues, particularly damaged body tissues. This term includes, in a non-limitative way, compounds that enhance wound healing ("wound healing agents"), scaring ("scaring agents") and compounds that enhance angiogenesis ("angiogenetic agents").

In a preferred embodiment, the tissue regenerating agent is extract from *Centella asiatica*. *Centella asiatica* (also known as gotu kola and Indian pennywort) is a perennial creeping plant which grows around the Indian ocean. Traditionally used in the management of dermatological conditions in its native area, it is used to support faster healing of small wounds, scratches and superficial burns, as well as an anti-inflammatory for eczema, minor itching and insect bites. The tissue regenerating activity of *Centella asiatica* is of particular relevance for repairing disturbed epithelial barrier (mayor wounds and/or microabrasions) in the vagina and/or cervix so as to avoid and/or combat persistent virus infection, for example HPV. In this sense, the combination of a tissue regenerating agent, such as *Centella Asiatica* extract, with *Coriolus versicolor* and, optionally, other active ingredients, is particularly effective. Thus in a particular embodiment the invention provides a composition comprising extract from *Coriolus versicolor* and extract from *Centella asiatica* for use in repairing disturbed vaginal or cervical epithelial barrier by vaginal or cervical administration. Another particular embodiment provides a composition comprising extract from *Coriolus versicolor* and extract from *Centella asiatica* for use in the prevention and/or clearance by vaginal or cervical administration of a vaginal and/or cervical persistent infection which is caused by an infectious agent as defined above, in particular persistent HPV infection.

"Extract from *Centella asiatica*" refers to an extract obtained from *Centella asiatica* which contains a high concentration of biologically-active compounds, particularly pentacyclic triterpenoids. Triterpenoids contained in these extracts are asiatic acid, madecassic acid and asiaticoside. "Extract from *Centella asiatica*" as used herein includes any of the available extracts from *Centella asiatica*, as well as purified or semi-purified preparations of biologically-active compounds from *Centella asiática* or a particular biologically-active compound obtained from *Centella asiatica*.

Clinical studies have been published describing the use of the following extracts from *Centella asiatica*: TTFCA, TECA and, where the name of the commercial extract is mentioned, Madecassol® (titrated extract of *Centella asiatica*) or Se® (total triterpenoid fraction of *Centella asiatica*) (EMA/HMPC/291177/200, 2010. "Assessment report on *Centella asiatica* (L.) Urban, herba"). Studies have shown that the main constituents of *Centella asiatica* increase collagen synthesis favouring tissue repair and angiogenesis.

In one embodiment the topical composition of the invention further comprises an antiviral agent "Antiviral agent" is understood in its general aception as a compound that may destroy or inhibit the development of viruses.

In a preferred embodiment, the antiviral agent is extract from *Azadirachta indica*. "*Azadirachta indica*", also known as Neem, Nimtree, and Indian Lilac is a tree in the mahogany family Meliaceae.

Various preparations of neem obtained from its different parts have been found to exert antibacterial, antiviral, antimalarial, antioxidant, antifungal, anti mutagenic, anticarcinogenic, contraceptive and antiulcer activity. The previous reports have documented that neem extracts significantly inhibited the polio virus, HIV, coxackie B group virus, and dengue virus at early step of viral genome replication (Tiwari V, et al. *Phytother Res*. 2010, vol. 24(8), p. 1132-1140).

Main chemical components are nimbin, nimbinene, azadirachtin, azadirachtol, azadirachnol, desacetynimbinene, nimbandiol, nimbolide, quercetin, beta-sitosterol, n-hexacosanol, nimbiol and nimocin. "Extract from *Azadirachta indica*" as used herein includes any of the available extracts from *Azadirachta indica*, as well as purified or semi-purified preparations of biologically-active compounds from *Azadirachta indica* or one particular biologically-active compound obtained from *Azadirachta indica*. These extracts are commercially available (for example may be obtained from the company Symrise).

In one embodiment the topical composition of the invention further comprises an antiinflammatory agent "Antiinflammatory agent" is understood in its general aception as a compound that that reduces inflammation. Preferably, the composition of the invention comprises antiinflammatory agents derived from natural sources. In a particular embodiment, the antiinflammatory agent derives from magnolia tree. In a preferred embodiment, the antiinflammatory agent is magnolol, honoliol or mixtures thereof. Magnolol (4-Allyl-2-(5-allyl-2-hydroxy-phenyl)phenol) and honokiol (2-(4-hydroxy-3-prop-2-enyl-phenyl)-4-prop-2-enyl-phenol) are lignans derived from magonlia tree that have been described to inhibit the nuclear factor kappa-light-chain-enhancer of activated B cells (NF-kB) and also to down regulate also the production of important inflammation mediators as the interleukin-8 (IL-8) and the tumor necrosis factor alpha (TNF-alpha).

In one embodiment the topical composition according to the invention comprises, in addition to extract from *C. versicolor*, a moisturizing agent, a prebiotic, an antiinflammatory agent, a tissue regenerating agent and, optionally, an antiviral agent and/or an antiinflammatory agent. In a particular embodiment, the composition of the invention comprises, in addition to extract of *C. versicolor*, hialuronic acid, bio-Ecolia® and extract from *Centella asiatica*. In another particular embodiment, the composition of the invention comprises, in addition to extract of *C. versicolor*, hialuronic acid, bio-Ecolia®, extract from *Centella asiatica* and extract from *Azadirachta indica*. In another particular embodiment, the composition of the invention comprises, in addition to extract of *C. versicolor*, hialuronic acid, bio-Ecolia®, extract from *Centella asiatica*, extract from *Azadirachta indica* magnolol and honokiol. In another embodiment the composition of the invention additionally comprises carboxymethyl beta-glucan.

In certain embodiments the composition of the invention comprises *C. versicolor* extract and at least one active compound selected from *Azadirachta indica* extract and a further beta-glucan (different from PSP and PSK beta-glucans contained in *C. versicolor* extract). The further beta-glucan can be selected from carboxylated beta-glucan, β(1,3)D-glucan and β(1,3)(1,4)-glucans from several natural sources. In a particular embodiment the further beta-glucan is carboxymethyl beta-glucan. In some embodiments the composition comprises *C. versicolor* extract, *Azadirachta indica* extract, a further beta-glucan (such as carboxymethyl beta-glucan) and at least one further active ingredient selected from a moisturizing agent, a prebiotic, an antiinflammatory agent, a tissue regenerating agent and aloe vera. In some embodiments the composition comprises *C. versicolor* extract, *Azadirachta indica* extract, a further beta-glucan (such as carboxymethyl beta-glucan) and at least one further active ingredient selected from hialuronic acid, alpha-glucan oligosaccharide, magnolol, honokiol, *Centella asiatica* extract and aloe vera. In a particular embodiment the composition of the invention comprises *Coriolus versicolor* extract, *Azadirachta* leaf extract, carboxymethyl beta-glucan, magnolol and honokiol. In a very particular embodiment the composition of the invention comprises *Coriolus versicolor* extract, *Azadirachta* leaf extract, carboxymethyl beta-glucan, hialuronic acid, Alpha-glucan oligosaccharide, magnolol, honokiol, *Centella asiatica* extract and aloe vera. The synergic combination of compounds in these compositions determines that they are particularly effective for use in the treatment and/or prevention of genital disorders caused by infectious agents, particularly against vaginitis and disorders caused by HPV infection, such as cervical cancer. In a particular embodiment the compositions as defined above are for use in repairing disturbed vaginal or cervical epithelial barrier by vaginal or cervical administration. Another particular embodiment provides a composition as defined above for use in curing vaginal lesions caused by an infectious agent, in particular LSIL or CIN1 lesions caused by HPV, by vaginal or cervical administration. Another particular embodiment provides a composition as defined above for use in the prevention and/or clearance by vaginal or cervical administration of a vaginal and/or cervical persistent infection which is caused by an infectious agent, in particular, persistent HPV infection.

Other components that may be incorporated in the compositions of the invention in addition to *C. versicolor* extract are extract from green tea leaf (or any of its well known biologically-active compounds), extract from *Melaleuca alternifolia* (or any of its well known biologically-active compounds) and aloe vera.

The present invention provides for topical compositions comprising an effective amount of the *C. versicolor* extract and/or an effective amount of biologically-active chemical constituents and/or compounds isolated from *C. versicolor*, preferably polysaccharopeptides PSK and/or PSP. In particular embodiments the topical compositions of the invention also contain an effective amount of at least one of the additional active ingredients described above (a moisturizing agent, a prebiotic, an antiinflammatory agent, a tissue regenerating agent, and an antiviral agent). The term "effective amount" as used herein, refers to the amount of a compound that, when administered, is sufficient to prevent development of, treat or alleviate to some extent the disorder which is addressed, which in the present invention is a genital disorder caused by an infectious agent. In the sense of the present invention an "effective amount" is also understood as the amount of compound that is sufficient to enhance genital immunity. For example, the effective amount of *C. versicolor* extract in the composition may be comprised from 0.005 to 5%, or from 0.01 to 1%, or from 0.01 to 0.5%, for example 0.02, 0.03, 0.04, 0.05, 0.06, 0.07, 0.08, 0.09, 0.1, 0.2, 0.3 or 0.4%. The effective amount of viral agent, such as *Azadirachta* extract, in the composition may be comprised from 0.001 to 5%, or from 0.005 to 1%, or from 0.005 to 0.1%, for example 0.006, 0.007, 0.008, 0.009, 0.01, 0.02, 0.03, 0.04, 0.05, 0.06, 0.07, 0.08 or 0.09%. The effective amount of further beta-glucan, such as carboxymethyl beta-glucan, in the composition may be comprised from 0.01 to 10%, or from 0.025 to 1%, or from 0.05 to 0.5%, for example 0.08, 0.08, 0.09, 0.1, 0.2, 0.3 or 0.4%. The effective amount of prebiotic, such as alpha-glucan oligosaccharide, in the composition may be comprised from 0.01 to 10%, or from 0.05 to 5%, or from 0.1 to 1%, for example 0.2, 0.3, 0.4, 0.5, 0.6, 0.7, 0.8 or 0.9%. The amount of moisturizing agent, such as hyaluronic acid, in the composition may be comprised from 0.01 to 10%, or from 0.05 to 5%, or from 0.1 to 1%, for example 0.2, 0.3, 0.4, 0.5, 0.6, 0.7, 0.8 or 0.9%. The effective amount of antiinflammatory agents, such as magnolol and/or honokiol, in the composition may be comprised from 0.005 to 5%, or from 0.01 to 2%, or from 0.05 to 1%, for example 0.06, 0.07, 0.08, 0.09, 0.1, 0.2, 0.3, 0.4, 0.5, 0.6, 0.7, 0.8 or 0.9%. The effective amount of tissue regenerating agent in the composition, such as compounds derived from *Centella asiatica* extract, in particular asiaticoside, madecassic acid and/or asiatic acid, may be comprised from 0.001 to 5%, or from 0.005 to 1%, or from 0.005 to 0.1%, for example 0.006, 0.007, 0.008, 0.009, 0.01, 0.02, 0.03, 0.04, 0.05, 0.06, 0.07, 0.08 or 0.09%. The composition may comprise aloe vera an amount comprised from 0.1 to 10%, or from 0.5 to 5%, for example 0.8, 1, 1.5, 2, 3 or 4%.

The particular dose of compound administered according to this invention will of course be determined by the particular circumstances surrounding the case, including the compound administered, the encapsulating efficiency, the route of administration, and similar considerations.

Preferably, the composition of the invention contains appropriate excipients and/or carriers for topical administration, which can be topically acceptable pharmaceutical or cosmetical excipients and carriers generally known in the state of the art. By "topically acceptable" as used herein refers to compounds, materials, compositions, and/or dosage forms which are, within the scope of sound medical judgement, suitable for use in contact with human and/or non-human animal skin and/or mucous membranes without undue toxicity, incompatibility, instability and allergic response, among others. Each "topically acceptable" carrier, excipient, etc., must also be "acceptable" in the sense of being compatible with the other ingredients of the formulation. Such excipients and carriers include, but are not limited to, agents for repairing cutaneous barrier function, hydrating agents, emollients, emulsifiers, thickeners, humectants, pH-regulating agents, antioxidants, preservative agents, vehicles, or their mixtures. The excipients and/or carriers used have affinity for the skin or mucus, are well tolerated, stable, and are used in an amount adequate to provide the desired consistency, and ease application. Additionally, the compositions may contain other ingredients, such as fragrances, colorants, and other components known in the state of the art for use in topical formulations.

The topical compositions of the invention may be suitable for pharmaceutical products. Said topical pharmaceutical compositions can be adapted to apply to the skin and mucosa in the form of: a non-ionic vesicular dispersion, emulsion, cream, lotion, gel, aerosol, cream-gel, gel-cream, suspension, dispersion, powder, solid stick, wipe, poultice, foam, spray, oil, ointment, fluid, soap, sanitary towel, ovule, pessary tampon, vaginal suppository or any other form that is known in the art of cosmetics and pharmacy. In a particular embodiment the composition of the invention is formulated as a gel and administered vaginally or cervically by means of a cannula.

Preferably, the topical composition of the invention is for genital administration, particularly to the vulva, vagina, cervix anus or rectum. A preferred embodiment of the invention provides for a topical composition comprising extract from *C. versicolor* that is for vaginal or cervical administration. Another preferred embodiment provides a topical composition for vaginal or cervical administration comprising extract from *C. versicolor* and at least an active compound selected from the group consisting of a moisturizing agent, a prebiotic, an antiinflammatory agent, a tissue regenerating agent, and an antiviral agent. Said compositions additionally contain excipients and/or carriers which are acceptable for vaginal or cervical administration. In other particular embodiments said preferred topical compositions may be administered in the form of a gel, a lotion, a soap, a cream, a foam, a sanitary towel, a wipe, an ovule, a pessary or a tampon.

Topical, including cervical or vaginal, formulations can be prepared according to methods well known in the state of the art. The appropriate carriers, and amounts thereof, can readily be determined by those skilled in the art according to the type of formulation being prepared. An exemplary topical composition for vaginal or cervical administration according to the invention may contain: water, aloe barbadensis leaf juice, glycerin, propanediol, hydroxyethylcellulose, hydrolyzed hyaluronic acid, sodium carboxymethyl betaglucan, alpha-glucan, oligosaccharide, *Coriolus versicolor* extract, *Azadirachta indica* leaf extract, watermelon seed oil polyglyceryl-6 esters, hazel seed oil polyglyceryl-6 esters, apricot kernel oil polyglyceryl-6 esters, kaempferol, polyglyceryl-10 dilaurate, lecithin, magnolol, honokiol, polyglyceryl-10 oleate, sorbitan oleate, sorbitan, palmitate, dicetyl phosphate, sodium benzoate, potassium sorbate, lactic acid.

Effectiveness of the compositions of the invention may be enhanced by encapsulating the active compounds into liposomes.

The term "liposome" is to be understood as a self-assembling structure comprising one or more membranes comprised by bilayers, each of which comprises two monolayers containing amphipathic molecules oppositely oriented. Amphipathic molecules may be polymers or lipids comprising a polar (hydrophilic) headgroup region covalently linked to one or more non-polar (hydrophobic) chains. Energetically unfavorable contacts between the hydrophobic acyl chains and the surrounding aqueous medium induce the amphipathic lipid molecules to arrange themselves such that their polar headgroups are oriented towards the bilayer's surface, while the acyl chains reorient towards the interior of the bilayer. An energetically stable structure is thus formed in which the acyl chains are effectively shielded from coming into contact with the aqueous environment.

A liposome encapsulates a region of aqueous solution inside a hydrophobic membrane; dissolved hydrophilic solutes cannot readily pass through the lipids. Hydrophobic chemicals can be dissolved into the membrane, and in this way liposome can carry both hydrophobic molecules and hydrophilic molecules. To deliver the molecules to sites of action, the lipid bilayer can fuse with other bilayers such as the cell membrane, thus delivering the liposome contents. The topical application of liposomes offers a wide range of advantages in cosmetics and pharmacy, including increased biodegradability, biocompatibility, as well as extended release and reduced toxicity and side effects of the encapsulated active agent. An further advantage is that the compositions comprising liposome-encapsulated active agents often show an extended shell-life, since the liposomes preserve said active agents from degradation.

Thus, in a particular embodiment, the extract from *C. versiculus* and/or one or more of the further active compounds comprised in the topical composition of the invention are encapsulated into liposomes.

Any type of liposome known in the state of the art can encapsulate the active compounds in the compositions of the invention. Particularly suitable types of liposomes are niosomes, phytosomes and nanosomes. Thus, in another particular embodiment, the extract from *C. versiculus* and/or one or more of the further active compounds comprised in the topical composition of the invention are encapsulated into niosomes, phytosomes and nanosomes.

A "niosome" is a non-ionic surfactant-based liposome. Niosomes are formed mostly by cholesterol incorporation as an excipient but other excipients can also be used. They are lamellar structures that are microscopic in size, constituted of non-ionic surfactant of the alkyl or dialkyl polyglycerol ether class and cholesterol with subsequent hydration in aqueous media. The materials used to prepare niosomes make them more stable and thus niosomes offer many advantages, for example, niosomes have a very high penetrating capability. Niosomes containing several biologically-active compounds are commercially available. For instance, hialuronic acid niosomes (NIO-Oligo HA®) are marketed by the company Naturalis Life Technologies. The same provider markets Nio-Glucan niosomes, which contain a mixture of carboxymethyl beta-glucan (a water soluble glucan derivative), magnolol and monokiol.

"Phytosomes" are a complex of a suitable molar ratio of a natural active ingredient and a phospholipid, preferably phosphatidylcholine, often containing also a polyphenol. A Phytosome, is a solid dispersion of an natural active ingredient or a mixture of active natural ingredients, for example a botanical extract, in a dietary phospholipid matrix, for example lecithin from soy. When encapsulated within a phytosome the active ingredient can somehow be compared to an integral part of the lipid membrane. Several natural active ingredients are commercially available in the form of phytosomes, for example, *Centella* Phytosome® containing triterpenes from *Centella asiatica* is readily available from Indena. The same provider also markets Greenselect® Phytosome®, which contains polyphenols from green tea leaf.

"Nanosomes" are nano-sized, single-bilayer liposomes containing a high percentage of phosphatidylcholine (PC). Nanosomes efficiently penetrate into the skin by topical application facilitating delivery of their encapsulated active compounds to the skin cells.

According to the invention the active compounds may be directly included in the composition or may be added in the form of liposomes. The invention also contemplates that some active compounds are included in the composition in the form of liposomes while others are not. Among the active compounds which are included in the composition in the form of liposomes, any type of convenient liposome, for example niosomes, phytosomes or nanosomes, or mixtures thereof is contemplated.

In a particular embodiment the topical composition of the invention comprises extract from *C. versicolor*, Nio-Oligo HA®, Bio-Ecolia®, *Centella* Phytosome® and, optionally, extract from *Azadirachta indica* and/or Nio-Glucan®.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following drawings are provided by way of illustration, and they are not intended to be limiting of the present invention. Furthermore, the present invention covers all possible combinations of particular and preferred embodiments described herein.

EXAMPLES

1. Formulation of a Topical Composition for Vaginal or Cervical Administration Comprising Extract from *Coriolus versicolor*

The following compostions was named PALOMA Gel Tópico Vulvo-Vaginal (PALOMA Gel) and contained the following components (% wt referred to the final composition):

0.5% alpha-glucan oligosaccharide, 0.18% sodium carboxymethyl betaglucan, 0.075% magnolol, 0.075% honokiol, 0.24% hydrolyzed hyaluronic acid, 0.04% kaempferol, 0.05% *Coriolus versicolor* extract, 0.01% *Azadirachta indica* extract, 0.013% asiaticoside, 0.012% madecassic acid, 0.008% asiatic acid, 1% Aloe barbadensis leaf juice, 8.8% glycerin, 6% propanediol, 1.2% hydroxyethylcellulose, 0.67% watermelon seed oil polyglyceryl-6 esters, 0.45% hazel seed oil polyglyceryl-6 esters, 0.45% polyglyceryl-10 dilaurate, 0.31% sodium benzoate, 0.3% apricot kernel oil polyglyceryl-6 esters, 0.241% hydroxypropyl guar, 0.24% polyglyceryl-10 oleate, 0.217% lecithin, 0.18% sorbitan oleate, 0.154% potassium sorbate, 0.096% lactic acid, 0.08% sorbitan palmitate, 0.8% dicetyl phosphate, 78.329% water.

This composition is in the form of a gel and may be administered inside the vagina or cervix by means of a cannula.

2. In Vitro Study

This study was designed to investigate if the composition of the invention is able to modulate the immune response of the vaginal epithelial tissues by assessing the cytokine release of the tissues into the basal compartment after defined treatment periods. The viability of the tissues was also assessed using MTT measurement.

Test System

The test was carried out with the reconstituted three-dimensional human vaginal epithelium model EpiVaginal™ VLC-100-FT (MatTek). The RhVE model EpiVaginal VLC-100-FT (MatTek) consists of normal human-derived VEC epithelial cells cultured atop a lamina propria-like collagen matrix that contains fibroblasts and dendritic cells (DC). The test system therefore represents in vitro the target organ of the species of interest and closely mimics the biochemical and physiological properties.

Materials

The following gels were tested:
PALOMA GEL composition of example 1 (P-7447)
VEHICLE gel composition of example 1 devoid of the following active ingredients: *C. versicolor* extract, *Azadirachta indica* extract, Carboxymethyl Beta-Glucan, Magnolol and Honokiol (P-7450).
VEHICLE+0.05% *C. versicolor* extract (P-7451)
VEHICLE+0.01% *Azadirachta indica* extract (P-7452)
VEHICLE+0.18% sodium carboxymethyl betaglucan, 0.075% magnolol, 0.075% honokiol (P-7453)
LPS Control (1 µg/mL Lipopolysaccharides, Sigma Cat No.: L4391)

The EpiVaginal™ tissues were provided as kits (VLC-100-FT, MatTek), consisting of the following components relevant for this study:
1× sealed 24-well plate containing 24 inserts with tissues on Agarose
1 bottle of assay medium (DMEM-based medium)
5. Further reagents
MTT Solution:
  MTT stock solution: 3 mg/mL MTT in PBS
  MTT medium: MTT stock solution will be diluted 1+9 with DMEM-based medium (final concentration 0.3 mg/mL)
Isopropanol Methodology a) Pre-Experiments To check the non-specific MTT-reducing capability of the test items 50 mg of the test item was mixed per 2 mL MTT medium and incubated for 3 h at 37±1° C. in the dark. If the mixture turns blue/purple, the test item was presumed to have reduced MTT. For quantitative correction of results, the part of absorption due to the non-specific reduction of MTT was be determined by using killed tissues. If non-specific MTT reduction is >30% relative to the negative control of living epidermis, the test item was considered as incompatible with the test method.

To check the colouring potential of the test items 50 mg of the test item was mixed per 90 µL aqua dest in a transparent recipient for 15 min. Criteria followed is if colouring is detected by unaided eye-assessment, the test item was checked for its tissue-colouring potential for quantitative correction of results by using additional viable tissues without MTT-staining. If non-specific OD due to coloration was >30% relative to the negative control, the test item was considered as incompatible with the test method.

b) Experimental Procedure

Upon receipt, the tissues were transferred into 24-well plates containing 0.6 mL prewarmed maintenance medium per well. The 24-well plates were incubated in a humidified incubator at 37±1° C., 5.0% $CO_2$ for at least 1 h and maximal 24 h. Then the medium was replaced by 0.6 ml fresh medium. Amounts of 50±2 mg (131.5 mg/cm$^2$) of the test item were weighed and applied onto the epithelium surface per each individual tissue. The test item was applied gently by repeated circular movements of the pipet to uniformly cover the tissue surface but avoiding any direct contact with the pipet tip. A nylon mesh can eventually be used for spreading.

6 h experiment: the tissues were treated with each dose group, starting with the negative control. Start time will be recorded with dosing of the first tissue. Then the tissues were incubated for 6 h 10 min at 37±1° C., 5.0% $CO_2$. 24 h experiment: the tissues were treated with each dose group, starting with the negative control. Start time was recorded with dosing of the first tissue. Then the tissues were incubated for 24 h±1 h at 37±1° C., 5.0% $CO_2$. After the respective incubation period the medium contacting the basal surface of the tissue was saved and store at −80° C. for further cytokine release analysis.

Then tissues were washed using e.g. a wash bottle be gently rinsed about 15 times with 25 mL PBS to remove any residual test item. Excess PBS was removed by gently shaking the insert and blotting bottom with blotting paper. All inserts were treated in the same manner.

Then treated tissues were transferred in a prepared 24-well plate containing 2 mL prewarmed MTT medium and further incubated for 3 h 5 min. at 37±1° C., 5.0% $CO_2$.

After the 3 h MTT incubation period the tissues were placed on blotting paper to dry the tissues. Afterwards a total biopsy of the epithelium by using special biopsy punched was performed. All tissue parts were transferred into suitable tubes and 500 μL of isopropanol was added. Extraction was carried out protected from light either over the weekend at 2-8° C. or, alternatively, at least 4 h at room temperature with vortexing of each tube at the middle of the incubation period.

If any visible cell/tissue fragments were in suspension, the tubes were centrifuged at 300×g to eliminate the fragments and avoid possible interference with the absorbance readings.

Per each tissue 2×200 μL aliquots of the extract were transferred into a 96-well plate and OD will be measured at 570 nm without reference wavelength in a plate spectrophotometer.

Cytokine determination was performed according to the manufacturer of the kit (V-PLEX Proinflammatory Panel1 (human) Kit, Meso Scale Discovery, Cat No: K15049D-1), Cytokines evaluated were IFN-gamma, IFN. Beta, IL-2, II-4, II-6, II-8, II-10, IL-12p70, IL-13 and TNF-alpha.

Results a) Irritant Potential of the Test Item

After an exposure time of 6 h and 24 h no cytotoxic effects could be observed when tissues are treated with PALOMA GEL (see table 1). The viability of the treated tissues was >50% (105% and 122%, at 6 and 24 respectively), compared to the negative control treated with PBS. Tissues treated with P-7450 (VEHICLE) showed lower viability of the treated tissues at 6 and 24 h compared to PALOMA GEL and negative control (PBS) but it was considered not irritant since viability was as well >50% (93% and 70% at 6 and 24 respectively).

These results might indicate, that neither PALOMA GEL nor the VEHICLE exhibit irritant effects.

TABLE 1

Viablility of human vaginal epithelium

| | Tissue Viability [%] | | |
|---|---|---|---|
| Name | 6 h exposure | 24 h exposure | |
| LPS Control 1 μg/ml | 95.7 | 112.9 | PC |
| P - 7447 | 105.8 | 122.9 | Complete Formulation |
| P - 7450 | 93.5 | 70.5 | Vehicle alone | b) Immunomodulatory Effect

To evaluate the potential immunomodulatory effect of the test samples, supernatant from treated tissues were collected and cytokine determination were performed according to the manufacturer of the kit (V-PLEX Proinflammatory Panel1 (human) Kit, Meso Scale Discovery, Cat No: K15049D-1).

Cytokines evaluated were the proinflammatory panel which included IFN-gamma, IFN. Beta, IL-2, II-4, II-6, II-8, II-10, IL-12p70, IL-13 and TNF-alpha.

As shown in table 2, an increase in the cytokines levels were observed after the treatment with the positive control LPS at the two concentrations tested (1 and 10 μg/ml). PALOMA GEL induced in most cases similar cytokine level that the positive control LPS at 1 μg/ml. Cytokines levels in tissues treated with P-7450 (VEHICLE) were lower in all cases.

TABLE 2

Cytokine levels in human vaginal epithelium

| Cytokines Final concentration (pg/mL) | 6 h | 24 h | % change |
|---|---|---|---|
| IFN Gamma | | | |
| P-7447 | 4.1 | 20.52 | 400% |
| P-7450 | 12.63 | 13.15 | 4% |
| P-7451 | 6.92 | 8.23 | 19% |
| P-7452 | 8.27 | 9.2 | 11% |
| P-7453 | 12.51 | 8.2 | −34% |
| LPS Control | 4.97 | 22.12 | 345% |
| IL-1Beta | | | |
| P-7447 | 9.45 | 24.31 | 157% |
| P-7450 | 18.27 | 21.37 | 17% |
| P-7451 | 12.27 | 16.18 | 32% |
| P-7452 | 13.76 | 17.26 | 25% |
| P-7453 | 13.45 | 19.25 | 43% |
| LPS Control | 11.49 | 31.09 | 171% |
| IL-2 | | | |
| P-7447 | 2.8 | 14.29 | 410% |
| P-7450 | 8.57 | 9.86 | 15% |
| P-7451 | 6.06 | 8.15 | 34% |
| P-7452 | 6.49 | 8.04 | 24% |
| P-7453 | 28.24 | 6.83 | −76% |
| LPS Control | 5.09 | 17.09 | 236% |
| IL-4 | | | |
| P-7447 | 0.8 | 2.55 | 219% |
| P-7450 | 1.75 | 1.67 | −5% |
| P-7451 | 1.07 | 1.18 | 10% |
| P-7452 | 1.22 | 1.12 | −8% |
| P-7453 | 1.4 | 1.27 | −9% |
| LPS Control | 0.83 | 2.75 | 231% |
| IL-6 | | | |
| P-7447 | 203 | 1087.58 | 436% |
| P-7450 | 735.8 | 780.61 | 6% |
| P-7451 | 392.88 | 394.88 | 1% |
| P-7452 | 574.2 | 402.5 | −30% |
| P-7453 | 501.15 | 367.27 | −27% |
| LPS Control | 355 | 1469 | 314% |
| IL-8 | | | |
| P-7447 | 9354 | 10222 | 9% |
| P-7450 | 9821 | 9859 | 0% |
| P-7451 | 9881 | 10047 | 2% |
| P-7452 | 9713 | 9763 | 1% |
| P-7453 | 10048 | 10110 | 1% |
| LPS Control | 9864 | 10707 | 9% |
| IL-10 | | | |
| P-7447 | 1.34 | 6.33 | 372% |
| P-7450 | 3.21 | 4.03 | 26% |
| P-7451 | 2.55 | 3.26 | 28% |
| P-7452 | 2.64 | 3.28 | 24% |
| P-7453 | 7.05 | 3.89 | −45% |
| LPS Control | 3.43 | 8.76 | 155% |
| IL-12p70 | | | |
| P-7447 | 1.97 | 6.83 | 247% |
| P-7450 | 4 | 4.27 | 7% |
| P-7451 | 3.31 | 3.76 | 14% |
| P-7452 | 2.81 | 2.93 | 4% |
| P-7453 | 4.7 | 5.12 | 9% |
| LPS Control | 2.67 | 8.92 | 234% |

TABLE 2-continued

Cytokine levels in human vaginal epithelium

| Cytokines Final concentration (pg/mL) | 6 h | 24 h | % change |
|---|---|---|---|
| IL-13 | | | |
| P-7447 | 36.14 | 85.23 | 136% |
| P-7450 | 54.48 | 69.41 | 27% |
| P-7451 | 40.42 | 61.5 | 52% |
| P-7452 | 52.78 | 65.02 | 23% |
| P-7453 | 61.19 | 67.71 | 11% |
| LPS Control | 46.17 | 101.22 | 119% |
| TNF-Alpha | | | |
| P-7447 | 3.16 | 14.87 | 371% |
| P-7450 | 8.69 | 10.6 | 22% |
| P-7451 | 5.92 | 7.71 | 30% |
| P-7452 | 7.37 | 9.03 | 23% |
| P-7453 | 22.25 | 6.5 | −71% |
| LPS Control | 6.6 | 24.89 | 277% |

Conclusions

A clear increase in cytokine levels ere observed at 24 hours compared to 6 hours in tissues treated with PALOMA GEL P-7447 and the positive control LPS indicating that immunostimulatory effect increased with the time up to 24 hours of treatment. No changes between 6 h and 24 hours have bean observed for the P-7450 VEHICLE. A synergic interaction is observed between the assayed active components of PALOMA GEL 3. Security Profile 3.1 Vaginal Irritation Test The composition of example 1 was assayed for vaginal irritation following ISO 10993-10:2010—Biological evaluation of medical devices part 10: tests for irritation and skin sensitization. The results indicated a vaginal irritation index of 0.00 for this composition. Thus, the composition of example 1 was considered not irritant for the vaginal mucosa membrane.

3.2 Cytotoxicity Test

The composition of example 1 was assayed for in vitro cytotoxicity following ISO 10993-5:2009 Biological evaluation of medical devices Part 5: Tests for in vitro cytotoxicity. Results indicated that mammal fibroblasts ATCC BalbC 3T3 treated with the composition of example 1 comprising extract from *C. versicolor* showed a cell viability reduction of 97.92%. Accordingly, the composition was considered cytotoxic.

3.3. Hypersensitivity Test

The composition of example 1 was assayed for skin hypersensitivity effect in guinea pigs following ISO 10993-10:2010 Biological evaluation of medical devices—Part 10: Tests for irritation and skin sensitization. No skin reactions were observed in the animals after challenge with the composition of example 1 comprising *C. versicolor* extract. These results indicate that the composition of example 1 may be considered not sensitizing.

4. In Vivo Studies 5.1. Immunomodulation in Mice

The aim of the study was to evaluate the immunomodulatory properties of the topical composition comprising *C. versicolor* extract after its local administration in the vagina of mice. This was performed in healthy mice. The local and systemic immune response was evaluated. Two different compositions were used, GEL 1 (PALOMA Gel with complete final formulation as disclosed in example 1) and GEL 2 (a formulation differing from that disclosed in example 1 in that the concentration of *Coriolus versicolor* extract is 0.25%).

This study was carried out in accordance with the 'Guide for the Care and Use of Laboratory Animals' as promulgated by the National Institute of Health, and the experimental protocols will be approved by the Local Ethic Committee of the University of Granada.

The study was performed among healthy mice obtained from Janvier (St Berthevin Cedex, France) and housed in makrolon cages (5 mice per cage) and maintained in an air-conditioned atmosphere with a 12-h light-dark cycle, and with free access to tap water and food. The mice were randomly assigned to the different experimental groups. Different groups (n=7) of female CBA/J (J-2α) healthy mice (8 to 10 weeks of age) were daily inoculated in the vagina with 50 μl of the GEL 1 or GEL 2. A control group (n=6) was inoculated PBS (control). Mice were sacrificed after 6 and 10 days of treatment to assess the effects of the treatment.

The vagina was excised for biochemical determinations to evaluate the local immune response by determining different cytokines (TNFα, IL-1β, IL-6, IL-12, IL-17) by RT-qPCR (Strum J et al, *Curr Protoc Pharmacol.*, 2002, Chapter 6: Unit 6.9), which will detect the amount of mRNA copies of each gene of interest. This technique consists on the amplification of the mRNA using a DNA template of the target gene to detect different patterns of transcription of the genes analyzed. The mRNA is first reverse transcribed to cDNA and then amplified. This is detected as the reaction progresses in "real time". To standardize the measurements, the target genes are studied in relation to another gene called a normalizing gene, which is selected for its almost constant level of expression. Glyceraldehyde-3-phosphate dehydrogenase (GAPDH), which is constitutively expressed, was used as housekeeping gene. The data thus generated was analyzed by computer software to calculate relative gene expression (or mRNA copy number) in several samples.

Figure 2:
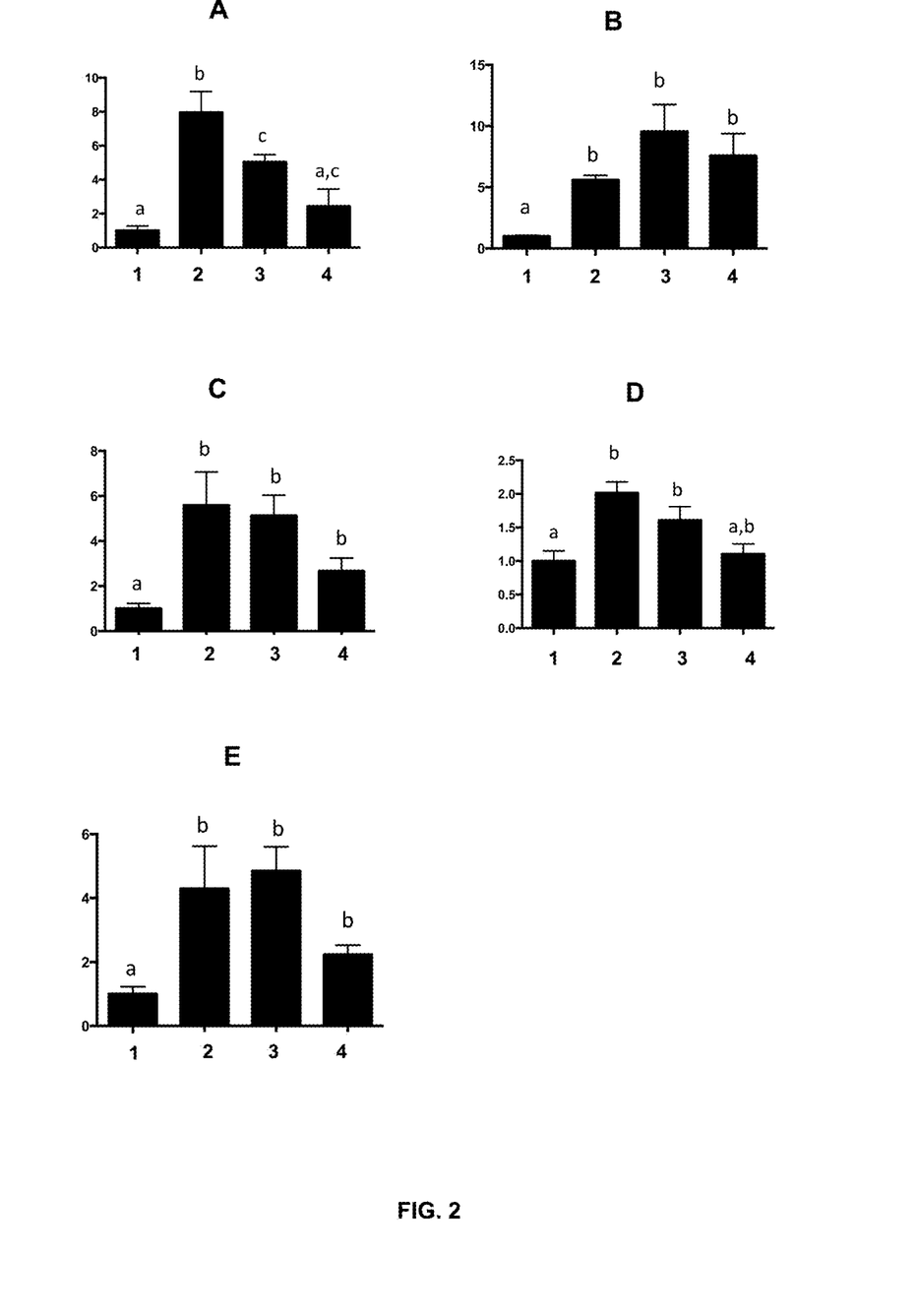
FIG. 2. Cytokine expression in vaginal epithelium as determined by RT-qPCR in mice after vaginal administration of control, GEL 1 (0.05% extract from *C. versicolor*) or GEL 2 (0.25% extract from *C. versicolor*). A: TNFα, B: IL-1β, C: IL-12, D: IL-6, E: IL-17. 1: control, 2: GEL 1 during 10 days, 3: GEL 2 during 6 days, 4: GEL 2 during 10 days. Y axis represents cytokine fold increase.

Results:

The results of the qPCR showed a significant ($p<0.05$) increase for all tested cytokines (TNFα, IL-1β, IL-6, IL-12, IL-17) in mice innoculated with GEL1 and also in mice innoculated with GEL2 at 10 days and 6 days vs Control group (FIG. 2). This indicates that the composition comprising *C. versicolor* extract, both at 0.05% and 0.25% concentration, activates the immune response of the vaginal epithelium's cells of healthy mice.

The immune response elicited by the extract of *Coriolus versicolor* (alone or in combination with further beta-glucans) is nonspecific. The nonspecific immune system, also known as the innate immune system, provides immediate defense against infection, and includes both humoral immunity components and cell-mediated immunity components. The major functions of the innate immune system include recruiting immune cells to sites of infection through the production of chemical factors, including cytokines. In this sense, while being nonspecific, the local nonspecific immune response elicited by the composition of the invention in healthy individuals/tissue may be extrapolated to individuals/tissue that are subject to an infection.

4.3. Vaginal Status and Cervical Epithelialization in Women.

The objective was to evaluate the effect of PALOMA GEL after 12 days of the gel application on: a) the changes of the vaginal microbiotical status, b) the degree of re-epithelialization of the cervix mucosa and c) the vaginal health status.

a) The vaginal microbiotical status was measured by the VaginalStatus test developed by the Institut für Mikroökologie. The VaginalStatus test differentiates between a bacterial or *Trichomonas vaginalis*-induced vaginitis and the organisms (*Lactobacillus*) present of an intact vaginal flora. The VaginalStatus control the following parameters:
Number of lactobacilli; incl. $H_2O_2$ producers
Number of β-B-streptococci
Number of Anaerobes
Vaginal Specific detection of *Trichomonas vaginalis* and *Atopobium*
Specific detection of *Gardnerella vaginalis*
Specific detection of yeasts (*Candida* spp.)
b) The effect on the epithelialization of the cervix mucosa was evaluated by standard colposcopy. Colposcopy lesions were rated by investigator using the CER Score (Cervix Epithelium Re-epithelialization Score):
5 . . . No ectopia
4 . . . Mild ectopia: <25% from periorificial orifice
3 . . . Moderate ectopia: Between a 25-50% from periorificial orifice
2 . . . Severe or extensive ectopia: >50% from periorificial orifice
1 . . . Severe ectopia+bleeding
c) The vaginal health status was assessed by the Bachmann Vaginal Health Index (VHI) (Bachmann G. "Urogenital ageing: an old problem newly recognized", *Maturitas* 1995, December; 22 Suppl: S1-S5; Bachman G. "A new option for managing urogenital atrophy in post menopausal women", *Contemp Obstet Gynecol* 1997, vol. 42, p. 13-28).

This study has been conducted on 11 healthy women (i.e, without clinical vaginal symptoms). Each patient received 12 days of Paloma gel vaginally once daily over night.

Vaginal microbiota data was obtained in 9 patients. Six of them presented some kind of infection at baseline (*Gardnerella vaginalis, Staphylococcus, E. coli, Mycoplasma, Streptococcus* beta-hemolytic and *Enterococcus* spp). At the end of the study, 5 (62%) women improved their vaginal microbiota condition and 2 out of them showed complete normalization. Two women demonstrated no significant improvement, although an increase of *Lactobacillus* was observed. One woman worsened her microbiota condition.

Colposcopy data was obtained for 11 women. Results in table 3 show a positive effect of the Paloma gel to improve the re-epithelialization of the cervix mucosa with a 24% of the improvement of the CER score. A total of 8 out of 11 women (72%) demonstrated a complete recovery (CER Score=5)

TABLE 3

Results of the Colposcopy evaluation (CER Score)

| CERS 1st VISIT | CERS 2nd VISIT |
|---|---|
| 4 | 5 |
| 4 | 5 |
| 4 | 5 |
| 3 | 5 |
| 5 | 5 |
| 4 | 5 |
| 3 | 4 |
| 4 | 5 |
| 4 | 5 |
| 3 | 4 |
| 4 | 4 |
| Mean 3.8 | Mean 4.72 (+24% improved vs 1st visit) |

Figure 3:
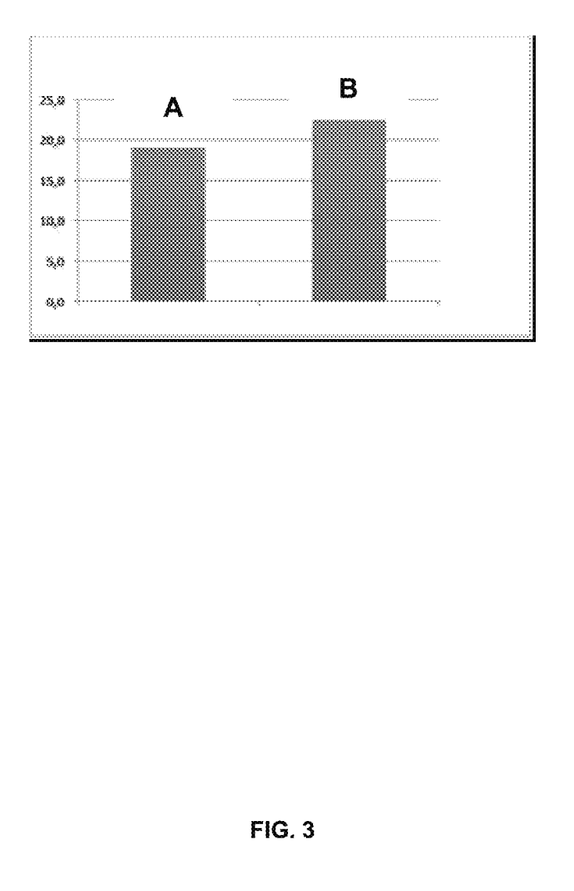
FIG. 3. Mean VHI value before PALOMA GEL application (column A) and after 12 days PALOMA GEL application (column B).

The VHI was evaluated in all women. The results showed a clear improvement in VHI. The mean total score increased a 18% at the end of the study (table 4 and FIG. 3)

TABLE 4

VHI results

| | VHI (T0) | VHI (T12) |
|---|---|---|
| 1 | 18 | 18 |
| 2 | 18 | 24 |
| 3 | 23 | 22 |
| 4 | 17 | 23 |
| 5 | 21 | 25 |
| 6 | 19 | 21 |
| 7 | 17 | 22 |
| 8 | 20 | 23 |
| 9 | 19 | 24 |
| 10 | 20 | 22 |
| 11 | 17 | 22 |
| Mean | 19.0 | 22.4 18% of improvement vs base line |

4.4. Cervical Epithelialization in Women.

This study has been conducted on 5 healthy women (i.e, without clinical vaginal symptoms). Each patient received 12 days of PALOMA GEL once daily over night. The effect on the epithelialization of the cervix mucosa was evaluated by standard colposcopy. Colposcopy lesions were rated using the CER Score (see above).

Results in table 2 show a positive effect of the PALOMA GEL to improve the re-epithelialization of the cervix mucosa with a 75% of the improvement of the CER score (baseline vs final: 2.4 vs 4.2). A total of 2 out of 5 women demonstrated a complete recovery (CER Score=5).

TABLE 2

Results of the Colposcopy evaluation (CER Score)

| PATIENT | COLPOSCOPY T0 | COLPOSCOPY T12 |
|---|---|---|
| 1 | 3 | 5 |
| 2 | 3 | 4 |
| 3 | 3 | 4 |
| 4 | 1 | 3 |
| 5 | 2 | 5 |
| Mean score | 2.4 | 4.2 (+75% vs T0) |

Figure 4:
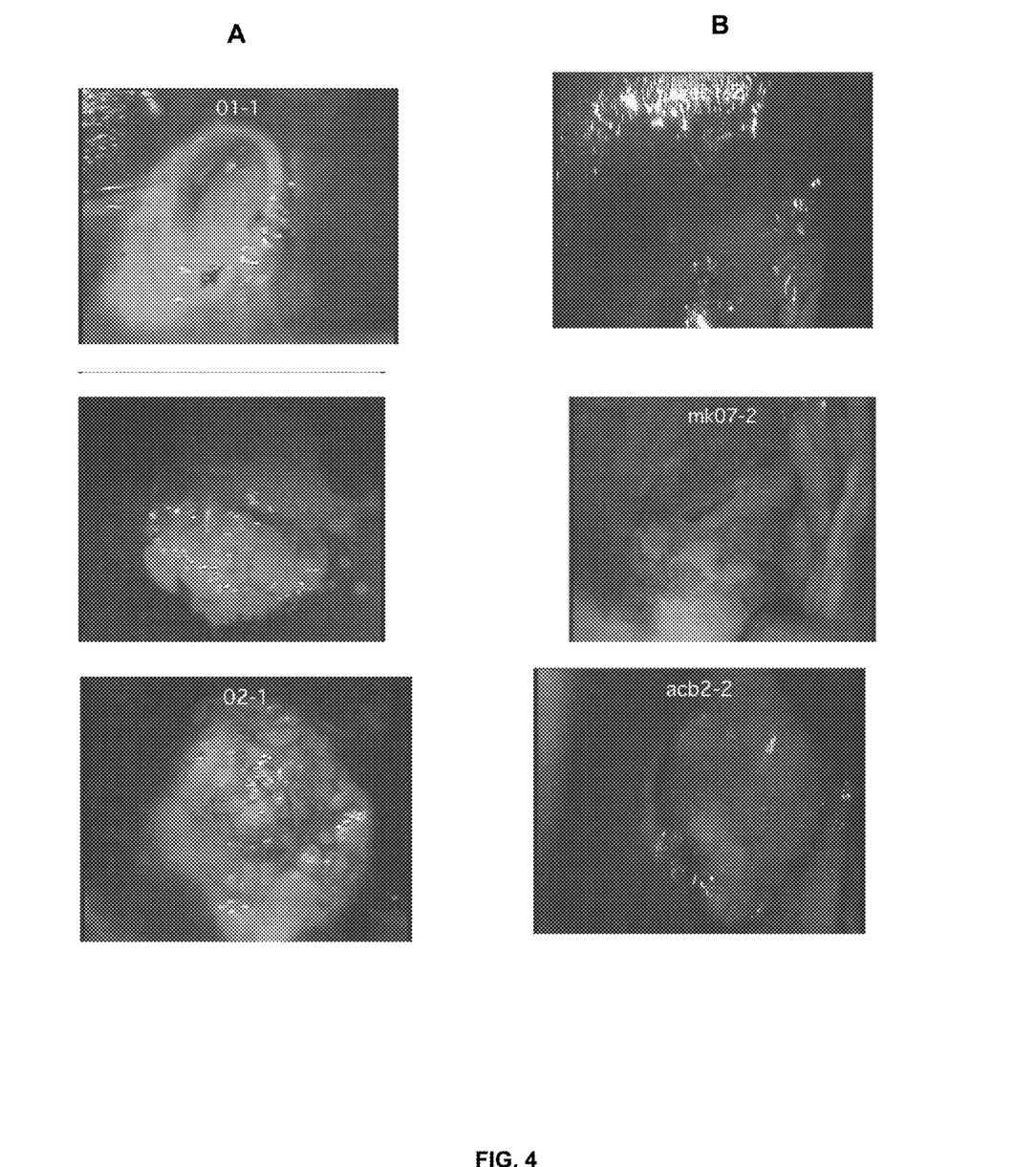
FIG. 4. Colposcopy pictures of 3 patients before PALOMA GEL application (column A) and after 12 days PALOMA GEL application (column B).

FIG. 4 shows the changes observed in the cervix mucosa. Dark areas correspond to epithelialization areas.

4.5. Pilot Clinical Study with HPV Positive Women

A "pilot", prospective, observational, parallel, comparative study was carried out to evaluate the effect of PALOMA Gel (see composition on example 1) on repairing injured vaginal mucosa in a women population with a positive Pap test for mild dysplasia (ASCUS, L-SIL, CIN-1). A total of 40 women, aged 18-65, were recruited. They were divided in 3 groups: PALOMA Gel administered once daily (n=15), PALOMA Gel administered every other day (n=15), and a control group with the standard management of these lesions, which amounts to no treatment being administered (n=15). Patients received PALOMA Gel or the standard management for 6 months and they were visited at baseline and after 3 and 6 months. An additional follow-up visit was performed at month 12 (after 6 months of no-treatment).

A colposcopy and a Pap test were performed on each visit. Data about reepithelization and state of vaginal lesions were obtained following standard proceedings. Subject preferences on regimens, quality of life and safety were collected in each visit. HPV genes L1 and E6/E7 were determined by PCR (L1), MT-PCT (E6/E7) and sequencing (L1) at baseline and at study termination to assess HPV infection.

Results

The baseline demographic and clinical characteristics were comparable in all groups.

At month 3, patients in both PALOMA Gel groups showed a trend to a better epithelialization of vaginal lesions compared to both, patients who received the standard management (intergroup comparison) and baseline (intragroup comparison). These differences were significant at month 6. The standard treatment showed a stationary or negative outcome on the repairing of vaginal lesions.

A slight trend to a greater negativization of HPV was observed in PALOMA Gel groups.

Likewise, a non-significant better outcome in quality of life scales was observed in patients under PALOMA Gel administration. No differences in regimen preferences were observed. Both PALOMA Gel regimens were safe throughout the study The obtained results are to be evaluated as entirely positive, considering the improvement in the clinical situation in the study groups (compared to the stationary or negative outcome in the control group) and also the almost total absence of side effects in the study groups This study indicates that PALOMA Gel administration is a good option in the management of mild vaginal lesions due to HPV.

5. Compositions of the Extracts and Other Products for Use in the Composition of the Invention Appropriate sources for the active ingredients employed in the compositions of the inventions are listed below.

C. versicolor extract (Actipone® Coriolus) from Symrise with the following composition: Water (>50%), Glycerin (25-50%), C. versicolor extract (1-5%), sodium benzoate (0.5%), lactic acid (0.215%) and potassium sorbate (0.2%).

Azadirachta indica extract (Extrapone® Neem) from Symrise with the following composition: Water (>50%), Glycerin (25-50%), Azadirachta indica extract (0.1-1%), sodium benzoate (0.5%), lactic acid (0.36%) and potassium sorbate (0.2%).

Prebiotic (Nio-Glucan®) from Naturalis Life Technologies with the following composition: Sodium Carboxymethyl Beta-Glucan: 2.0-6.0%, Magnolol/Honokiol: 1.0-3.0%, Polyglyceryl-10 Dilaurate: 10.0-15.0%, Watermelon Seed Oil Polyglyceryl-6 Ester 10.0-15.0%, Hazel Seed Oil Polyglyceryl-6 Ester 10.0-15.0%, Sorbitan Oleate: 4.0-6.0%, Lecithin: 3.0-5.0%, Water 45.0-50.0%

REFERENCES CITED IN THE APPLICATION

Kang S C et al. "Effects of β-glucans from *Coriolus versicolor* on macrophage phagocytosis are related to the Akt and CK2/Ikaros", *Int J Biol Macromol.* 2013, vol. 57, p. 9-16.

Cui J, et al. "Polysaccharopeptides of *Coriolus versicolor* physiological activity, uses, and production". *Biotechnol Adv.* 2003, vol. 21(2), p. 109-22.

K F Cheng, et al. "General review of polysaccharopeptides from. *C. versicolor*: Pharmacological and clinical studies", *Cancer Therapy* 2008, vol. 6, p. 117-130.

EMA/HMPC/291177/200, 2010. "Assessment report on *Centella asiatica* (L.) Urban, herba".

Tiwari V, et al. "In vitro antiviral activity of neem (*Azadirachta indica* L.) bark extract against herpes simplex virus type-1 infection". *Phytother Res.* 2010, vol. 24(8), p. 1132-1140

ISO 10993-10:2010—Biological evaluation of medical devices part 10: tests for irritation and skin sensitization ISO 10993-5:2009 Biological evaluation of medical devices Part 5: Tests for in vitro cytotoxicity Strum J et al. "Tissue expression profiling using real-time PCR", *Curr Protoc Pharmacol.* 2002, Chapter 6: Unit 6.9, doi: 10.1002/0471141755.ph0609s18.

Bachmann G. "Urogenital ageing: an old problem newly recognized", *Maturitas* 1995, December; 22 Suppl: S1-S5

Bachman G. "A new option for managing urogenital atrophy in post menopausal women", *Contemp Obstet Gynecol* 1997, vol. 42, p. 13-28

CLAUSES

1. A topical composition comprising an extract from *Coriolus versicolor*, for use in the prevention and/or treatment by genital administration of a genital disorder which is caused by an infectious agent.

2. The topical composition according to clause 1, wherein the prevention and/or treatment comprises enhancing genital immunity against infectious agents.

3. The topical composition according to any of the clauses 1-2, wherein the genital administration is vaginal or cervical administration.

4. The topical composition for use according to any of the clauses 1-3, wherein the infectious agent is selected from the group consisting of human papiloma virus (HPV), *Candida albicans, Chlamydia trachomatis, Gardnerella vaginalis, Mobiluncus, Bacteroides, Mycoplasma, Neisseria gonorrhoeae, Trichomonas vaginalis*, Herpes virus, *Staphylococcus aureus, Staphylococcus epidermis, Escherichia coli, Streptococcus alpha, Bacillus, Enterobacter, Proteus, Enterobacter cloacae, Klebsiella, S. epidermidis, Klebsiella pneumoniae* and dermatophytes.

5. The topical composition for use according to clause 4, wherein the infectious agent is human papiloma virus.

6. The topical composition for use according to any of the clauses 1-5, wherein the genital disorder is selected from the group consisting of cervical cancer, vulvovaginitis, dermatophytosis, candidiasis, genital herpes, gonorrhoea, proctitis, infertility, cervicitis, pelvic inflammatory disease, ectopic pregnancy, acute or chronic pelvic pain, trichomoniasis.

7. The topical composition for use according to clause 6, wherein the genital disorder is cervical cancer.

8. A topical composition for genital administration comprising extract from *Coriolus versicolor*.

9. The topical composition according to clause 8, wherein the genital administration is vaginal or cervical administration.

10. The topical composition according to any of the clauses 8-9, further comprising at least an active compound selected from the group consisting of a moisturizing agent, a prebiotic, a tissue regenerating agent, an antiinflammatory agent and an antiviral agent.

11. The topical composition according to clause 10, which comprises as further active compounds a moisturizing agent, a prebiotic and a tissue regenerating agent.

12. The topical composition according to clause 11, which further comprises an antiinflammatory agent and/or an antiviral agent.

13. The topical composition according to any of the clauses 10-12, wherein the moisturizing agent is hialuronic acid, the prebiotic is bio-Ecolia®, the tissue regenerating agent is extract from *Centella asiatica*, the antiviral agent is extract from *Azadirachta indica* and the antiinflammatory agent is selected from magnolol, honokiol and mixtures thereof.

14. The topical composition according to any of the clauses 10-13, wherein the extract from *Coriolus versiculus* and/or one or more of the further active compounds are encapsulated into liposomes.

15. The topical composition according to any of the clauses 10-14, which comprises extract from *Coriolus versicolor*, Nio-Oligo HA®, Bio-Ecolia® and *Centella* Phytosome®.

The invention claimed is:

1. A method for the prevention and/or treatment of a vaginal or cervical disorder in a subject in need thereof, comprising administering vaginally or cervically a composition comprising an extract from *Coriolus versicolor*, wherein the vaginal or cervical disorder is caused by an infectious agent selected from the group consisting of: human papiloma virus (HPV), *Candida albicans*, *Chlamydia trachomatis*, *Gardnerella vaginalis*, *Mobiluncus*, *Bacteroides*, *Mycoplasma*, *Neisseria gonorrhoeae*, *Trichomonas vaginalis*, Herpes virus, *Staphylococcus aureus*, *Staphylococcus epidermis*, *Escherichia coli*, *Streptococus alfa*, *Bacillus*, *Enterobacter*, *Proteus*, *Enterobacter cloacae*, *Klebsiella*, *S. epidermidis*, *Klebsiella pneumoniae* and dermatophytes.

2. The method according to claim 1, wherein the infectious agent is human papiloma virus (HPV).

3. The method according to claim 1, wherein the vaginal or cervical disorder is selected from the group consisting of cervical cancer, vulvovaginitis, dermatophytosis, candidiasis, genital herpes, gonorrhoea, proctitis, infertility, cervicitis, pelvic inflammatory disease, ectopic pregnancy, acute or chronic pelvic pain, and trichomoniasis.

4. The method according to claim 1, wherein the vaginal or cervical disorder is cervical cancer.

5. The method according to claim 1, wherein the treatment comprises curing vaginal epithelial lesions caused by the infectious agent.

6. The method according to claim 1, wherein the treatment comprises clearance of the infection.

7. The method according to claim 1, wherein the subject suffers from low scuamous intraepithelial lesion (LSIL) or mild cervical intraepithelial neoplasia (CIN1).

8. The method according to claim 1, wherein the composition further comprises an active compound selected from the group consisting of a moisturizing agent, a prebiotic, an antiinflammatory agent, a tissue regenerating agent and an antiviral agent.

* * * * *